US012595461B2

(12) United States Patent
Ryu et al.

(10) Patent No.: US 12,595,461 B2
(45) Date of Patent: Apr. 7, 2026

(54) **MICROORGANISM OF *CORYNEBACTERIUM* GENUS HAVING ENHANCED L-ARGININE OR L-CITRULLINE PRODUCTIVITY AND A METHOD FOR PRODUCING L-ARGININE OR L-CITRULLINE USING THE SAME**

(71) Applicant: DAESANG CORPORATION, Seoul (KR)

(72) Inventors: Mi Ryu, Gyeonggi-do (KR); Sun Jun Yoon, Gyeonggi-do (KR); In Pyo Hong, Gyeonggi-do (KR); Seok Hyun Park, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 468 days.

(21) Appl. No.: 17/937,828

(22) Filed: Oct. 4, 2022

(65) Prior Publication Data

US 2024/0026282 A1        Jan. 25, 2024

(30) Foreign Application Priority Data

Jul. 21, 2022        (KR) ........................ 10-2022-0090642

(51) Int. Cl.
| | |
|---|---|
| *C12N 1/20* | (2006.01) |
| *C12N 1/205* | (2026.01) |
| *C12R 1/15* | (2006.01) |

(52) U.S. Cl.
CPC .......... *C12N 1/205* (2021.05); *C12R 2001/15* (2021.05)

(58) Field of Classification Search
CPC ...... C12N 1/205; C12N 9/1217; C12N 15/77; C12N 1/20; C12R 2001/15; C12P 13/10; C12Y 207/02008
See application file for complete search history.

(56) References Cited

U.S. PATENT DOCUMENTS 8,048,648 B2 * 11/2011 Kim ........................ C12P 13/10
435/114

FOREIGN PATENT DOCUMENTS

| | | |
|---|---|---|
| CN | 106434594 | 2/2017 |
| EP | 1 801 206 | 6/2007 |

| | | | | |
|---|---|---|---|---|
| EP | 1801206 A1 * | 6/2007 | ..... | C12Y 207/02008 |
| JP | 2017-79705 | 5/2017 | | |
| KR | 2004-0073176 | 1/2005 | | |
| KR | 10-2008-0006799 | 1/2008 | | |
| KR | 10-0830290 | 5/2008 | | |
| KR | 10-2269637 | 6/2021 | | |
| WO | 2006/035831 | 4/2006 | | |

OTHER PUBLICATIONS

Xu M, Rao Z, Dou W, Jin J, Xu Z. Site-directed mutagenesis studies on the L-arginine-binding sites of feedback inhibition in N-acetyl-L-glutamate kinase (NAGK) from Corynebacterium glutamicum. Current microbiology. Feb. 2012;64:164-72. (Year: 2012).*

Livingstone CD, Barton GJ. Protein sequence alignments: a strategy for the hierarchical analysis of residue conservation. Bioinformatics. Dec. 1, 1993;9(6):745-56. (Year: 1993).*

Notice of Reasons for Refusal dated Aug. 28, 2023 in corresponding Japanese Patent Application No. 2022-162572, with English-language translation.

Ikeda M. et al., "Reengineering of a *Corynebacterium glutamicum* L-Arginine and L-Citrulline Producer.", Applied and Environmental Microbiology, Mar. 2009, vol. 75, No. 6, p. 1635-1641.

Park et al., "Metabolic engineering of *Corynebacterium glutamicum* for *L*-arginine production", Nature communications, Aug. 2014, vol. 5, Article No. 4618, pp. 1-9.

Extended European Search Report issued May 19, 2023 in European Application No. 22200152.1.

Office Action issued May 30, 2024 in Korean Patent Application No. 10-2022-0090642, with English-language Translation.

Masato Ikeda, et al., "Reengineering of a *Corynebacterium glutamicum* *L*-Arginine and *L*-Citrulline Producer", Applied and Environmental Microbiology, Mar. 2009, vol. 75, No. 6, pp. 1635-1641.

* cited by examiner

*Primary Examiner* — Jennifer M.H. Tichy
*Assistant Examiner* — Emily F Eix
(74) *Attorney, Agent, or Firm* — Wenderoth, Lind & Ponack, L.L.P.

(57) ABSTRACT

The present disclosure relates to a *Corynebacterium* sp. mutant strain having increased L-arginine or L-citrulline productivity and a method of producing L-arginine or L-citrulline using the same. The *Corynebacterium* sp. mutant strain has enhanced activity of acetylglutamate kinase involved in the L-arginine biosynthesis pathway, and thus is capable of producing L-arginine or L-citrulline in an increased yield compared to a parent strain.

3 Claims, 3 Drawing Sheets

Specification includes a Sequence Listing.

SEQUENCE LISTING

```
Sequence total quantity: 22
SEQ ID NO: 1              moltype = DNA  length = 885
FEATURE                   Location/Qualifiers
source                    1..885
                          mol_type = genomic DNA
                          organism = Corynebacterium sp.
SEQUENCE: 1
ttgcagcact tccgcgacaa gattgttgtc gtgaaatatg gcggaaacgc catggtggat  60
gatgatctca aggctgcttt tgctgccgac atggtcttct tgcgcaccgt gggcgcaaaa  120
ccagtggtgg tgcacggtgg tggacctcag atttctgaga tgctaaaccg tgtgggtctc  180
cagggcgagt tcaagggtgg tttccgtgtg accactcctg aggtcatgga cattgtgcgc  240
atggtgctct ttggtcaggt cggtcgcgat ttagttggtt tgatcaactc tcatggccct  300
tacgctgtgg gaacctccgg tgaggatgcc ggcctgttta ccgcgcagaa gcgcatggtc  360
aacatcgatg gcgtacccac tgatattggt ttggtcggag acatcattaa tgtcgatgcc  420
tcttccttga tggatatcat cgaggccggt cgcattcctg tggtctctac gattgctcca  480
ggcgaagacg gccagattta caacattaac gccgataccg cagcaggtgc tttggctgca  540
gcgattggtg cagaacgcct gctggttctc accaatgtgg aaggtctgta caccgattgg  600
cctgataaga gctcactggt gtccaagatc aaggccaccg agctggaggc cattcttccg  660
ggacttgatt ccggcatgat tccaaagatg gagtcttgct tgaacgcggt gcgtggggga  720
gtaagcgctg ctcatgtcat tgacggccgc atcgcgcact cggtgttgct ggagcttttg  780
accatgggtg gaattggcac gatggtgctg ccggatgttt ttgatcggga gaattatcct  840
gaaggcaccg tttttagaaa agacgacaag gatggggaac tgtaa               885

SEQ ID NO: 2              moltype = AA  length = 294
FEATURE                   Location/Qualifiers
source                    1..294
                          mol_type = protein
                          organism = Corynebacterium sp.
SEQUENCE: 2
MQHFRDKIVV VKYGGNAMVD DDLKAAFAAD MVFLRTVGAK PVVVHGGGPQ ISEMLNRVGL  60
QGEFKGGFRV TTPEVMDIVR MVLFGQVGRD LVGLINSHGP YAVGTSGEDA GLFTAQKRMV  120
NIDGVPTDIG LVGDIINVDA SSLMDIIEAG RIPVVSTIAP GEDGQIYNIN ADTAAGALAA  180
AIGAERLLVL TNVEGLYTDW PDKSSLVSKI KATELEAILP GLDSGMIPKM ESCLNAVRGG  240
VSAAHVIDGR IAHSVLLELL TMGGIGTMVL PDVFDRENYP EGTVFRKDDK DGEL         294

SEQ ID NO: 3              moltype = DNA  length = 885
FEATURE                   Location/Qualifiers
source                    1..885
                          mol_type = other DNA
                          organism = synthetic construct
SEQUENCE: 3
ttgcagcact tccgcgacaa gattgttgtc gtgaaatatg gcggaaacgc catggtggat  60
gatgatctca aggctgcttt tgctgccgac atggtcttct tgcgcaccgt gggcgcaaaa  120
```

```
ccagtggtgg tgcacggtgg tggacctcag atttctgaga tgctaaaccg tgtgggtctc  180
cagggcgagt tcaagggtgg tttccgtgtg accactcctg aggtcatgga cattgtgcgc  240
atggtgctct ttggtcaggt cggtcgcgat ttagttggtt tgatcaactc tcatggccct  300
tacgctgtgg gaacctccgg tgaggatgcc ggcctgttta ccgcgcagaa gcgcatggtc  360
aacatcgatg gcgtacccac tgatattggt ttggtcggag acatcattaa tgtcgatgcc  420
tcttccttga tggatatcat cgaggccggt cgcattcctg tggtctctac gattgctcca  480
ggcgaagacg gccagattta caacattaac gccgataccg cagcaggtgc tttggctgca  540
gcgattggtg cagaacgcct gctggttctc accaatgtgg aaggtctgta caccgattgg  600
cctgataaga gctcactggt gtccaagatc aaggccaccg agctggaggc cattcttccg  660
ggacttgatt ccggcatgat tccaaagatg gagtcttgct tgaacgcggt gcgtggggga  720
gtaagcgctg ctcatgtcat tgacggccgc atcgcgcact cggtgttgct gctgctttttg  780
accatgggtg gaattggcac gatggtgctg ccggatgttt ttgatcggga gaattatcct  840
gaaggcaccg ttttttagaaa agacgacaag gatgggggaac tgtaa            885
```

```
SEQ ID NO: 4              moltype = AA   length = 294
FEATURE                   Location/Qualifiers
source                    1..294
                          mol_type = protein
                          organism = synthetic construct
SEQUENCE: 4
MQHFRDKIVV VKYGGNAMVD DDLKAAFAAD MVFLRTVGAK PVVVHGGGPQ ISEMLNRVGL  60
QGEFKGGFRV TTPEVMDIVR MVLFGQVGRD LVGLINSHGP YAVGTSGEDA GLFTAQKRMV  120
NIDGVPTDIG LVGDIINVDA SSLMDIIEAG RIPVVSTIAP GEDGQIYNIN ADTAAGALAA  180
AIGAERLLVL TNVEGLYTDW PDKSSLVSKI KATELEAILP GLDSGMIPKM ESCLNAVRGG  240
VSAAHVIDGR IAHSVLLLLL TMGGIGTMVL PDVFDRENYP EGTVFRKDDK DGEL       294
```

```
SEQ ID NO: 5              moltype = DNA   length = 885
FEATURE                   Location/Qualifiers
source                    1..885
                          mol_type = other DNA
                          organism = synthetic construct
SEQUENCE: 5
ttgcagcact tccgcgacaa gattgttgtc gtgaaatatg gcggaaacgc catggtggat  60
gatgatctca aggctgcttt tgctgccgac atggtcttct tgcgcaccgt gggcgcaaaa  120
ccagtggtgg tgcacggtgg tggacctcag atttctgaga tgctaaaccg tgtgggtctc  180
cagggcgagt tcaagggtgg tttccgtgtg accactcctg aggtcatgga cattgtgcgc  240
atggtgctct ttggtcaggt cggtcgcgat ttagttggtt tgatcaactc tcatggccct  300
tacgctgtgg gaacctccgg tgaggatgcc ggcctgttta ccgcgcagaa gcgcatggtc  360
aacatcgatg gcgtacccac tgatattggt ttggtcggag acatcattaa tgtcgatgcc  420
tcttccttga tggatatcat cgaggccggt cgcattcctg tggtctctac gattgctcca  480
ggcgaagacg gccagattta caacattaac gccgataccg cagcaggtgc tttggctgca  540
gcgattggtg cagaacgcct gctggttctc accaatgtgg aaggtctgta caccgattgg  600
cctgataaga gctcactggt gtccaagatc aaggccaccg agctggaggc cattcttccg  660
ggacttgatt ccggcatgat tccaaagatg gagtcttgct tgaacgcggt gcgtggggga  720
gtaagcgctg ctcatgtcat tgacggccgc atcgcgcact cggtgttgct ggcgcttttg  780
accatgggtg gaattggcac gatggtgctg ccggatgttt ttgatcggga gaattatcct  840
gaaggcaccg ttttttagaaa agacgacaag gatgggggaac tgtaa            885
```

```
SEQ ID NO: 6              moltype = AA   length = 294
FEATURE                   Location/Qualifiers
source                    1..294
                          mol_type = protein
                          organism = synthetic construct
SEQUENCE: 6
MQHFRDKIVV VKYGGNAMVD DDLKAAFAAD MVFLRTVGAK PVVVHGGGPQ ISEMLNRVGL  60
QGEFKGGFRV TTPEVMDIVR MVLFGQVGRD LVGLINSHGP YAVGTSGEDA GLFTAQKRMV  120
NIDGVPTDIG LVGDIINVDA SSLMDIIEAG RIPVVSTIAP GEDGQIYNIN ADTAAGALAA  180
AIGAERLLVL TNVEGLYTDW PDKSSLVSKI KATELEAILP GLDSGMIPKM ESCLNAVRGG  240
VSAAHVIDGR IAHSVLLALL TMGGIGTMVL PDVFDRENYP EGTVFRKDDK DGEL       294
```

```
SEQ ID NO: 7              moltype = DNA   length = 885
FEATURE                   Location/Qualifiers
source                    1..885
                          mol_type = other DNA
                          organism = synthetic construct
SEQUENCE: 7
ttgcagcact tccgcgacaa gattgttgtc gtgaaatatg gcggaaacgc catggtggat  60
gatgatctca aggctgcttt tgctgccgac atggtcttct tgcgcaccgt gggcgcaaaa  120
ccagtggtgg tgcacggtgg tggacctcag atttctgaga tgctaaaccg tgtgggtctc  180
cagggcgagt tcaagggtgg tttccgtgtg accactcctg aggtcatgga cattgtgcgc  240
atggtgctct ttggtcaggt cggtcgcgat ttagttggtt tgatcaactc tcatggccct  300
tacgctgtgg gaacctccgg tgaggatgcc ggcctgttta ccgcgcagaa gcgcatggtc  360
aacatcgatg gcgtacccac tgatattggt ttggtcggag acatcattaa tgtcgatgcc  420
tcttccttga tggatatcat cgaggccggt cgcattcctg tggtctctac gattgctcca  480
ggcgaagacg gccagattta caacattaac gccgataccg cagcaggtgc tttggctgca  540
gcgattggtg cagaacgcct gctggttctc accaatgtgg aaggtctgta caccgattgg  600
cctgataaga gctcactggt gtccaagatc aaggccaccg agctggaggc cattcttccg  660
ggacttgatt ccggcatgat tccaaagatg gagtcttgct tgaacgcggt gcgtggggga  720
gtaagcgctg ctgatgtcat tgacggccgc atcgcgcact cggtgttgct ggagctttttg  780
```

-continued

```
accatgggtg gaattggcac gatggtgctg ccggatgttt ttgatcggga gaattatcct    840
gaaggcaccg tttttagaaa agacgacaag gatgggggaac tgtaa                    885

SEQ ID NO: 8               moltype = AA   length = 294
FEATURE                    Location/Qualifiers
source                     1..294
                           mol_type = protein
                           organism = synthetic construct
SEQUENCE: 8
MQHFRDKIVV VKYGGNAMVD DDLKAAFAAD MVFLRTVGAK PVVVHGGGPQ ISEMLNRVGL    60
QGEFKGGFRV TTPEVMDIVR MVLFGQVGRD LVGLINSHGP YAVGTSGEDA GLFTAQKRMV    120
NIDGVPTDIG LVGDIINVDA SSLMDIIEAG RIPVVSTIAP GEDGQIYNIN ADTAAGALAA    180
AIGAERLLVL TNVEGLYTDW PDKSSLVSKI KATELEAILP GLDSGMIPKM ESCLNAVRGG    240
VSAADVIDGR IAHSVLLELL TMGGIGTMVL PDVFDRENYP EGTVFRKDDK DGEL          294

SEQ ID NO: 9               moltype = DNA   length = 33
FEATURE                    Location/Qualifiers
source                     1..33
                           mol_type = other DNA
                           organism = synthetic construct
SEQUENCE: 9
tgattacgcc actgacacgg tggataagga aac                                  33

SEQ ID NO: 10              moltype = DNA   length = 23
FEATURE                    Location/Qualifiers
source                     1..23
                           mol_type = other DNA
                           organism = synthetic construct
SEQUENCE: 10
actgacacgg tggataagga aac                                             23

SEQ ID NO: 11              moltype = DNA   length = 18
FEATURE                    Location/Qualifiers
source                     1..18
                           mol_type = other DNA
                           organism = synthetic construct
SEQUENCE: 11
agcagcaaca ccgagtgc                                                   18

SEQ ID NO: 12              moltype = DNA   length = 20
FEATURE                    Location/Qualifiers
source                     1..20
                           mol_type = other DNA
                           organism = synthetic construct
SEQUENCE: 12
ggtcaaaagc agcagcaaca                                                 20

SEQ ID NO: 13              moltype = DNA   length = 28
FEATURE                    Location/Qualifiers
source                     1..28
                           mol_type = other DNA
                           organism = synthetic construct
SEQUENCE: 13
gcttttgacc atgggtggaa ttggcacg                                       28

SEQ ID NO: 14              moltype = DNA   length = 18
FEATURE                    Location/Qualifiers
source                     1..18
                           mol_type = other DNA
                           organism = synthetic construct
SEQUENCE: 14
atgggtggaa ttggcacg                                                  18

SEQ ID NO: 15              moltype = DNA   length = 18
FEATURE                    Location/Qualifiers
source                     1..18
                           mol_type = other DNA
                           organism = synthetic construct
SEQUENCE: 15
catcgggaac aacgccat                                                  18

SEQ ID NO: 16              moltype = DNA   length = 19
FEATURE                    Location/Qualifiers
source                     1..19
                           mol_type = other DNA
                           organism = synthetic construct
SEQUENCE: 16
atggtcacca catcgggaa                                                 19
```

-continued

```
SEQ ID NO: 17          moltype = DNA  length = 16
FEATURE                Location/Qualifiers
source                 1..16
                       mol_type = other DNA
                       organism = synthetic construct
SEQUENCE: 17
gccagcaaca ccgagt                                            16

SEQ ID NO: 18          moltype = DNA  length = 20
FEATURE                Location/Qualifiers
source                 1..20
                       mol_type = other DNA
                       organism = synthetic construct
SEQUENCE: 18
ggtcaaaagc gccagcaaca                                        20

SEQ ID NO: 19          moltype = DNA  length = 21
FEATURE                Location/Qualifiers
source                 1..21
                       mol_type = other DNA
                       organism = synthetic construct
SEQUENCE: 19
caatgacatc agcagcgctt a                                      21

SEQ ID NO: 20          moltype = DNA  length = 17
FEATURE                Location/Qualifiers
source                 1..17
                       mol_type = other DNA
                       organism = synthetic construct
SEQUENCE: 20
atgcggccgt caatgac                                           17

SEQ ID NO: 21          moltype = DNA  length = 28
FEATURE                Location/Qualifiers
source                 1..28
                       mol_type = other DNA
                       organism = synthetic construct
SEQUENCE: 21
acggccgcat cgcgcactcg gtgttgct                               28

SEQ ID NO: 22          moltype = DNA  length = 18
FEATURE                Location/Qualifiers
source                 1..18
                       mol_type = other DNA
                       organism = synthetic construct
SEQUENCE: 22
cgcgcactcg gtgttgct                                          18
```

MICROORGANISM OF *CORYNEBACTERIUM* GENUS HAVING ENHANCED L-ARGININE OR L-CITRULLINE PRODUCTIVITY AND A METHOD FOR PRODUCING L-ARGININE OR L-CITRULLINE USING THE SAME

SEQUENCE LISTING

A sequence listing in electronic (XML file) format is filed with this application and incorporated herein by reference. The name of the ASCII text file is "AttachG_Sequencelist_1901.XML"; the file was created on Oct. 4, 2022; the size of the file is 24,873 bytes.

BACKGROUND

1. Technical Field

The present disclosure relates to a *Corynebacterium* sp. microorganism having increased L-arginine or L-citrulline productivity and a method of producing L-arginine or L-citrulline using the same.

2. Related Art

Arginine is known to be contained in plants and the like in a free state. Arginine is one of the non-essential amino acids, but in growing children and special conditions such as stress, trauma, and cancer, it is considered a semi-essential amino acid that should be necessarily supplied, and is widely used as a component for amino acid supplements, pharmaceuticals, foods, and the like. For medicine, arginine is used in liver function promoters, brain function promoters, male infertility treatment agents, comprehensive amino acid preparations, and the like, and for food, arginine is used as a fish cake additive, a health drink additive, and a salt substitute for hypertensive patients.

Citrulline is one of the non-essential amino acids, and it is known that citrulline has useful effects such as promoting ammonia metabolism, improving blood flow by vasodilation, lowering blood pressure, neurotransmission, enhancing immunity, and scavenging reactive oxygen species. In the kidney, citrulline is metabolized to arginine, from which nitric oxide (NO) is produced. That is, citrulline is not an amino acid constituting a protein in vivo, but is one of the intermediates of the urea cycle, and is produced from arginine together with NO, which is known as a substance having a vasodilatory action. In addition, citrulline is condensed with aspartic acid and regenerated into arginine.

The production of such arginine and citrulline may be performed using a naturally occurring wild-type strain or a mutant strain modified from the wild-type strain so as to have increased arginine or citrulline productivity. Recently, in order to increase the efficiency of production of arginine or citrulline, genetic recombination technology has been used for microorganisms such as *Escherichia coli* and *Corynebacterium*. In biosynthesis of L-arginine in microorganisms, L-glutamate is used as a starting material and converted sequentially into N-acetylglutamate, N-acetylglutamyl-P, N-acetylglutamate 5-semialdehyde, N-acetylornithine, L-ornithine, L-citrulline, and argininosuccinate, thereby synthesizing L-arginine. Various proteins such as enzymes, transcription factors, and transport proteins are involved in this stepwise synthesis process. Therefore, it is possible to increase L-arginine or L-citrulline productivity by regulating the activities of various proteins, which are involved in the biosynthesis of L-arginine or L-citrulline, through genetic recombination technology, and many studies have been required to develop a recombinant strain or mutant strain having excellent L-arginine or L-citrulline productivity.

PRIOR ART DOCUMENTS

Patent Documents

Korean Patent No. 10-2269637

SUMMARY

An object of the present disclosure is to provide a *Corynebacterium* sp. mutant strain having increased L-arginine or L-citrulline productivity.

Another object of the present disclosure is to provide a method of producing L-arginine or L-citrulline using the mutant strain.

One aspect of the present disclosure provides a *Corynebacterium* sp. mutant strain having increased L-arginine or L-citrulline productivity by having enhanced activity of acetylglutamate kinase.

"Acetylglutamate kinase" used in the present disclosure serves to catalyze a reaction that converts N-acetylglutamate into N-acetylglutamyl-P in the L-arginine biosynthesis pathway. The N-acetylglutamate is sequentially converted into other substances by various enzymes, and as a result, is synthesized into L-arginine or L-citrulline.

According to one embodiment of the present disclosure, the acetylglutamate kinase may be derived from a *Corynebacterium* sp. microorganism.

More specifically, the *Corynebacterium* sp. microorganism may be *Corynebacterium glutamicum*, *Corynebacterium crudilactis*, *Corynebacterium deserti*, *Corynebacterium callunae*, *Corynebacterium suranareeae*, *Corynebacterium lubricantis*, *Corynebacterium doosanense*, *Corynebacterium efficiens*, *Corynebacterium uterequi*, *Corynebacterium stationis*, *Corynebacterium pacaense*, *Corynebacterium singulare*, *Corynebacterium humireducens*, *Corynebacterium marinum*, *Corynebacterium halotolerans*, *Corynebacterium spheniscorum*, *Corynebacterium freiburgense*, *Corynebacterium striatum*, *Corynebacterium canis*, *Corynebacterium ammoniagenes*, *Corynebacterium renale*, *Corynebacterium pollutisoli*, *Corynebacterium imitans*, *Corynebacterium caspium*, *Corynebacterium testudinoris*, *Corynebacaterium pseudopelargi*, or *Corynebacterium flavescens*, without being limited thereto.

As used herein, the term "enhanced activity" means that expression of genes encoding proteins of interest, such as enzymes, transcription factors and transport proteins, has been newly introduced or has been increased so that the expression levels of the proteins have increased compared to those in a wild-type strain or a strain before modification. The term "enhanced activity" also includes: a case in which the activity of the proteins themselves has increased compared to the activity of the proteins, originally possessed by the microorganism, through substitutions, insertions, deletions or combinations thereof, of one or more nucleotides in nucleotide sequences encoding the genes; a case in which the overall activity of the enzymes in the cell is higher than that in the wild-type strain or the strain before modification due to increased expression or translation of the genes encoding the enzymes; and a combination thereof.

According to one embodiment of the present disclosure, enhancement of the activity of the acetylglutamate kinase may be achieved by site-directed mutation in a gene encoding the acetylglutamate kinase.

According to one embodiment of the present disclosure, the gene encoding acetylglutamate kinase may be represented by the nucleotide sequence of SEQ ID NO: 1 or may consist of the amino acid sequence of SEQ ID NO: 2.

According to one embodiment of the present disclosure, the site-directed mutation may be a substitution of one or more nucleotides in the nucleotide sequence of SEQ ID NO: 1.

According to one embodiment of the present disclosure, the site-directed mutation may be a substitution of one or more amino acids in the amino acid sequence of SEQ ID NO: 2.

More specifically, the site-directed mutation may be a consecutive or non-consecutive substitution of one, two, three, four, or five amino acids at positions 50 to 400 or 100 to 300 in the amino acid sequence of SEQ ID NO: 2.

According to one embodiment of the present disclosure, the site-directed mutation may be a substitution of a non-polar amino acid for glutamic acid at amino acid position 258 in the amino acid sequence of SEQ ID NO: 2.

The non-polar amino acid has a hydrophobic R group composed of a non-polar hydrocarbon, and thus does not bond with a polar water molecule. In addition, the non-polar amino acid has low chemical reactivity, and is located in the three-dimensional structure of a globular protein.

The non-polar amino acid in the present disclosure may be one selected from the group consisting of glycine, alanine, valine, leucine, isoleucine, proline, phenylalanine, methionine and tryptophan, and is preferably alanine, isoleucine, leucine or valine, which may exhibit a similar three-dimensional protein structure.

According to one embodiment of the present disclosure, the site-directed mutation may be a substitution of aspartic acid for histidine at amino acid position 245 in the amino acid sequence of SEQ ID NO: 2.

Due to this enhancement of the acetylglutamate kinase activity by this mutation, feedback inhibition of acetylglutamate kinase may be inhibited or released, so that the arginine biosynthesis pathway may be enhanced, and consequently, L-arginine or L-citrulline productivity may be increased.

As used herein, the term "increased productivity" means that L-arginine or L-citrulline productivity has increased compared to that in the parent strain. As used herein, the term "parent strain" refers to a wild-type strain or mutant strain to be mutated, and includes a strain that is to be mutated directly or to be transformed with a recombinant vector or the like. In the present disclosure, the parent strain may be a wild-type *Corynebacterium* sp. microorganism or a microorganism or strain mutated from the wild-type microorganism.

As described above, the *Corynebacterium* sp. mutant strain having increased L-arginine or L-citrulline productivity according the present disclosure contains the mutated nucleotide sequence or amino acid sequence of the gene encoding acetylglutamate kinase, and thus exhibits increased L-arginine or L-citrulline productivity compared to the parent strain. In particular, the L-arginine or L-citrulline productivity of the *Corynebacterium* sp. mutant strain may be at least 5%, specifically 5 to 80%, 5 to 30%, or 30 to 70% higher than that of the parent strain.

According to one embodiment of the present disclosure, the *Corynebacterium* sp. mutant strain may be *Corynebacterium glutamicum*.

The *Corynebacterium* sp. mutant strain according to one embodiment of the present disclosure may be obtained through a recombinant vector containing a variant having a substitution of a portion of the sequence of acetylglutamate kinase in the parent strain.

As used herein, the term "portion" means not all of the nucleotide sequence, the polynucleotide sequence, or the amino acid sequence, and may be 1 to 300, preferably 1 to 100, more preferably 1 to 50, without being limited thereto.

As used herein, the term "variant" refers to a polypeptide that differs from the amino acid sequence of a protein encoding a specific gene before mutation due to conservative substitutions, deletions, modifications or additions of one or more amino acids at the N-terminus, C-terminus of and/or within the amino acid sequence, but retains functions or properties of the protein. As used herein, the term "conservative substitution" means replacing one amino acid with another amino acid having similar structural and/or chemical properties. The conservative substitution may have little or no impact on the activity of the resulting protein or polypeptide. In addition, the variant includes those in which one or more portions, such as an N-terminal leader sequence or transmembrane domain, have been removed. Furthermore, the variant includes those in which a portion has been removed from the N- and/or C-terminus of a mature protein. The ability of the variant may be increased, unchanged, or reduced compared to that of the polypeptide before mutation. In the present disclosure, the term "variant" may be used interchangeably with terms such as mutant, modification, variant polypeptide, modified protein, mutation, and the like.

According to one embodiment of the present disclosure, the acetylglutamate kinase variant may have the amino acid sequence of SEQ ID NO: 4, 6 or 8.

As used herein, the term "vector" means an expression vector capable of expressing a protein of interest in an appropriate host cell, and refers to a gene construct comprising essential regulatory elements that are operably linked to a transgene so that the transgene is expressed. As used herein, the term "operably linked" means that a gene to be expressed is functionally linked to regulatory sequences therefor in a manner that allows for expression of the gene. "Regulatory elements" include a promoter for effecting transcription, an optional operator sequence for regulating transcription, a sequence encoding suitable mRNA ribosome binding sites, and sequences which control termination of transcription and translation. Examples of the vector include, but are not limited to, a plasmid vector, a cosmid vector, a bacteriophage vector, a viral vector, and the like. Example of the phage vector or cosmid vector that may be used include pWE15, M13, ΔEMBL3, ΔEMBL4, ΔFIXII, ΔDASHII, ΔZAPII, Agt10, Agtll, Charon4A, and Charon21A, and examples of the plasmid vector that may be used include a pDZ vector, and pBR-based, pUC-based, pBluescriptll-based, pGEM-based, pTZ-based, pCL-based and pET-based vectors. A vector that may be used is not particularly limited, and any known expression vector may be used without limitation.

After the "recombinant vector" used in the present disclosure is transformed into a suitable host cell, it may optionally replicate and function independently of the host genome, or in some cases may be integrated into the genome itself. In this case, the "suitable host cell" is one in which the vector is replicable, and may include an origin of replication, which is a specific nucleotide sequence from which replication begins.

The transformation may be performed using a suitable vector introduction technique selected depending on the host cell, and the gene of interest may be expressed in the host cell. For example, vector introduction may be performed by electroporation, heat shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or combinations thereof. The transformed gene may include any gene, regardless of whether the gene is inserted into the chromosome of the host cell or located outside of the chromosome, as long as the gene may be expressed in the host cell.

The host cell includes a cell transfected, transformed, or infected with the recombinant vector or polynucleotide of the present disclosure in vivo or in vitro. The host cell including the recombinant vector of the present disclosure is a recombinant host cell, a recombinant cell, or a recombinant microorganism.

In addition, the recombinant vector according to the present disclosure may contain a selection marker. The selection marker is used to select transformants (host cells) transformed with the vector. Since only cells expressing the selection marker can survive in a medium treated with the selection marker, it is possible to select the transformed cells. Representative examples of the selection marker include, but are not limited to, kanamycin, streptomycin, chloramphenicol, and the like.

Genes inserted into the recombinant vector for transformation according to the present disclosure may be integrated into a host cell such as a *Corynebacterium* sp. microorganism by homologous recombination crossover.

According to one embodiment of the present disclosure, the host cell may be a *Corynebacterium* sp. strain, for example, a *Corynebacterium glutamicum* strain.

Another aspect of the present disclosure provides a method for producing L-arginine or L-citrulline comprising steps of: culturing the *Corynebacterium glutamicum* mutant strain in a medium; and recovering L-arginine or L-citrulline from the cultured mutant strain or the medium in which the mutant strain has been cultured.

The culturing may be performed using a suitable medium and culture conditions known in the art, and any person skilled in the art may easily adjust and use the medium and the culture conditions. Specifically, the medium may be a liquid medium, but is not limited thereto. Examples of the culturing method include, but are not limited to, batch culture, continuous culture, fed-batch culture, or a combination thereof.

According to one embodiment of the present disclosure, the medium should meet the requirements of a specific strain in a proper manner, and may be appropriately modified by a person skilled in the art. For the culture medium for the *Corynebacterium* sp. microorganism or strain, reference may be made to, but not limited to, a known document (Manual of Methods for General Bacteriology, American Society for Bacteriology, Washington D.C., USA, 1981).

According to one embodiment of the present disclosure, the medium may contain various carbon sources, nitrogen sources, and trace element components. Examples of carbon sources that may be used include: saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, without being limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present disclosure, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present disclosure, in the step of recovering L-arginine or L-citrulline from the cultured mutant strain and the medium in which the mutant strain has been cultured, the produced L-arginine or L-citrulline may be collected or recovered from the medium using a suitable method known in the art depending on the culture method. Examples of the method for recovering L-arginine or L-citrulline that may be used include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present disclosure, the step of recovering L-arginine or L-citrulline may be performed by centrifuging the culture medium at a low speed to remove biomass and separating the obtained supernatant through ion-exchange chromatography.

According to one embodiment of the present disclosure, the step of recovering L-arginine or L-citrulline may include a process of purifying L-arginine or L-citrulline.

The *Corynebacterium* sp. mutant strain according to the present disclosure has enhanced activity of the acetylglutamate kinase involved in the L-arginine biosynthesis pathway, and thus is capable of producing L-arginine or L-citrulline in an increased yield compared to the parent strain.

TABLE 1

|  |  | Primer (5'→3') | SEQ ID NO |
|---|---|---|---|
| Amplification | argB-F1 | tgattacgcc actgacacggtggataaggaaac | 9 |
| primers for left | argB-F2 | actgacacggtggataaggaaac | 10 |
| homologous arm of | E258L-R1 | agcagcaacaccgagtgc | 11 |
| argB | E258L-R2 | ggtcaaaagcagcagcaaca | 12 |
| | | | |
| Amplification | E258L-F1 | gcttttgacc atgggtggaattggcacg | 13 |
| primers for right | E258L-F2 | atgggtggaattggcacg | 14 |
| homologous arm of | argB-R1 | catcgggaacaacgccat | 15 |
| argB | argB-R2 | atggtcaccacatcgggaa | 16 | having a substitution of alanine for glutamic acid at amino acid position 258 according to one embodiment of the present disclosure.

Figure 3:
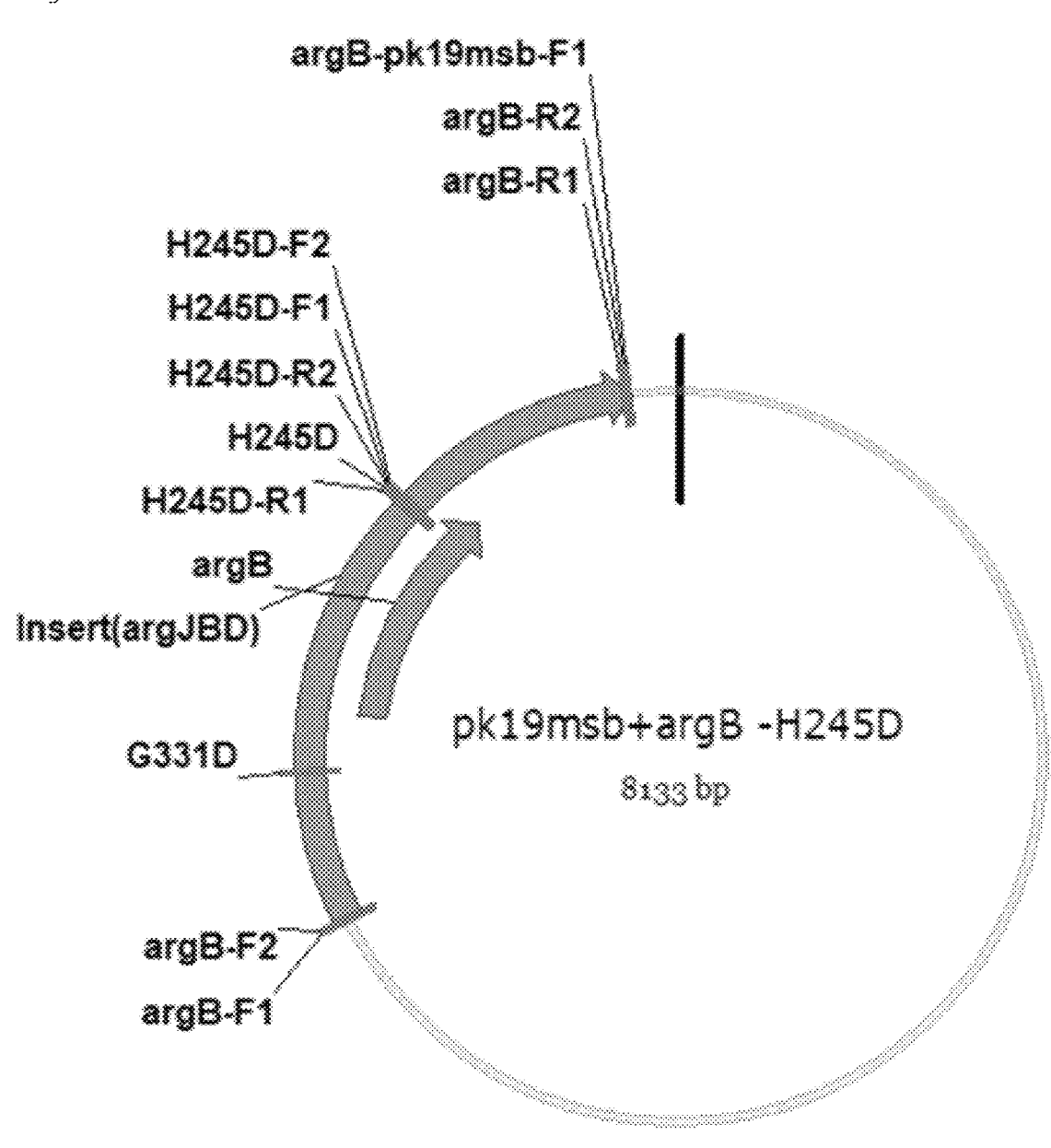

FIG. 3 shows the structure of a pk19msb+argB-H245D vector containing a gene encoding an acetylglutamate kinase having a substitution of aspartic acid for histidine at amino acid position 245 according to one embodiment of the present disclosure.

DETAILED DESCRIPTION

Hereinafter, the present disclosure will be described in more detail. However, these descriptions are provided for illustrative purposes only to aid in the understanding of the present disclosure, and the scope of the present disclosure is not limited by these illustrative descriptions.

Example 1. Construction of *Corynebacterium glutamicum* Mutant Strain

To construct a *Corynebacterium glutamicum* mutant strain having enhanced activity of acetylglutamate kinase, *Corynebacterium glutamicum* 14GR (KCCM13219P) strain, which is an L-arginine-producing strain, and *E. coli* DH5a (HIT Competent Cells™, Cat No. RH618) were used.

The *Corynebacterium glutamicum* 14GR strain was cultured in an ARG-broth medium (pH 7.2) containing 10.5 g of 98% glucose, 1 g of beef extract, 4 g of yeast extract, 2 g of polypeptone, 2 g of NaCl and 40 g of $(NH_4)_2SO_4$ in 1 L of distilled water at a temperature of 30° C.

The *E. coli* DH5a was cultured on an LB medium containing 10.0 g of tryptone, 10.0 g of NaCl and 5.0 g of yeast extract in 1 L of distilled water at a temperature of 37° C.

The antibiotic kanamycin used was the product of Sigma. DNA sequencing was performed by Macrogen, Inc.
1-1. Recombinant Vector Mutation was induced in acetylglutamate kinase to enhance the biosynthesis pathway in the strain. In the method used in this Example, the argB gene encoding acetylglutamate kinase was subjected to site-directed mutagenesis in order to increase expression of the gene. Glutamic acid at amino acid position 258 of the acetylglutamate kinase encoded by the argB gene was substituted with leucine, and the left arm portion (1,614 bp) and the right arm portion (854 bp) with respect to the center of the argB gene on the *Corynebacterium glutamicum* genome were ampli- Using the above-described primers, PCR was performed under the following conditions. PCR was performed using a Thermocycler (TP600, TAKARA BIO Inc., Japan) in a reaction solution containing 100 μM of each deoxynucleotide triphosphate (dATP, dCTP, dGTP, dTTP), 1 μM oligonucleotide, 10 ng of the chromosomal DNA of *Corynebacterium glutamicum* ATCC 13032 as a template, and 1 unit of pfu-X DNA polymerase mixture (Solgent). PCR was performed for 25 to 30 cycles, each consisting of (i) denaturation at 94° C. for 30 sec, (ii) annealing at 58° C. for 30 sec, and (iii) extension at 72° C. for 1 to 2 min (a polymerization time of 2 min per kb).

The gene fragments prepared as described above were cloned into a pk19msb vector by self-assembly cloning. The vector was transformed into *E. coli* DH5a which was then plated on an LB-agar plate containing 50 μg/ml of kanamycin, and cultured at 37° C. for 24 hours. The finally formed colony was isolated and whether the insert was exactly present in the vector was checked. Next, the vector was isolated and used for recombination of the *Corynebacterium glutamicum* strain.

As a process commonly performed in the above method, the corresponding genes were amplified by PCR from the genomic DNA of *Corynebacterium glutamicum* ATCC 13032 and inserted into the pk19msb vector by the self-assembled cloning method according to the strategy, and the resulting plasmid was selected in *E coli* DH5a. For chromosomal base substitution, the gene fragments were amplified individually and ligated together by overlap PCR, thereby preparing the desired DNA fragment. For genetic manipulation, Ex Taq polymerase (Takara) and Pfu polymerase (Solgent) were used as PCR polymerases, and various restriction enzymes and DNA modifying enzymes purchased from NEB were used, and they were used according to manufacturer's provided buffers and protocols.
1-2. *Corynebacterium glutamicum* Mutant Strain AB1

Mutant strain AB1 was constructed using a cloning vector. The cloning vector was prepared at a final concentration of 1 μg/μl or more and electroporated into a *Corynebacterium glutamicum* 14GR strain (see Tauch et al., FEMS Microbiology letters 123 (1994) 343-347) to induce first recombination. In this case, the electroporated strain was plated on an agar medium containing 50 μg/μl of kanamycin, colonies were isolated, and then whether the vector was properly inserted at the desired position on the genome was checked by PCR and sequencing. Each of the isolated strains was inoculated again in a liquid medium to induce second recombination, cultured overnight or more, and then plated on an agar medium containing 10% sucrose, and colonies were isolated. Whether the finally isolated colonies were resistant to kanamycin was checked, and then whether mutation was introduced into the acetylglutamate kinase in the strains having no antibiotic resistance was checked by sequencing (see Schafer et al., Gene 145 (1994) 69-73). As a result, *Corynebacterium glutamicum* mutant strain AB1 capable of producing L-arginine was constructed, which has a substitution of leucine for glutamic acid at position 258 in the amino acid sequence of acetylglutamate kinase (SEQ ID NO: 2).

Example 2. Construction of *Corynebacterium glutamicum* Mutant Strain

A *Corynebacterium glutamicum* mutant strain having enhanced activity of acetylglutamate kinase was constructed in the same manner as in Example 1, a recombinant vector (pk19msb+argB-E258A) containing an argB gene encoding an acetylglutamate kinase having a substitution of alanine for glutamic acid at amino acid position 258 was used.

Figure 1:
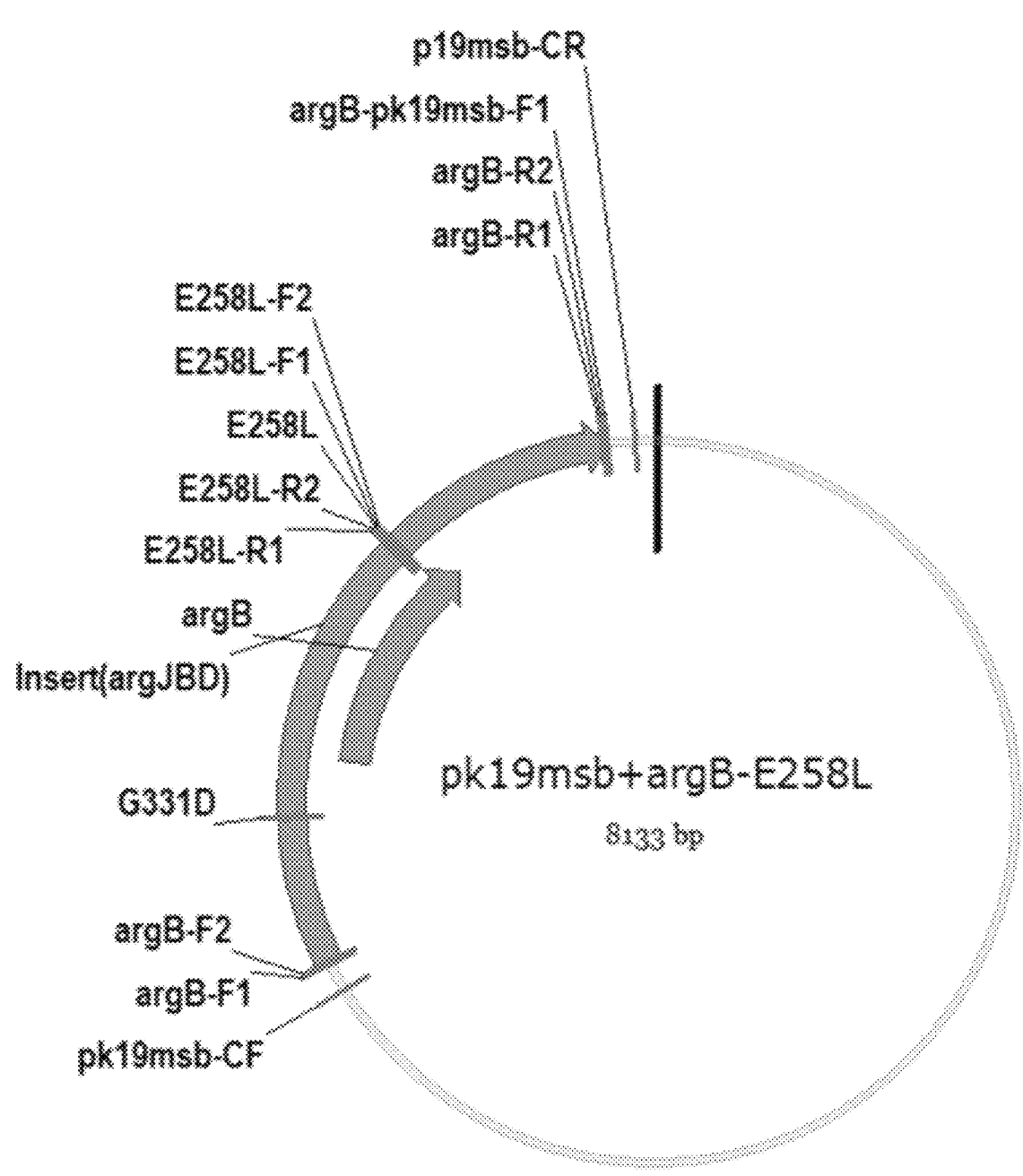
FIG. 1 shows the structure of a pk19msb+argB-E258L vector containing a gene encoding an acetylglutamate kinase having a substitution of leucine for glutamic acid at amino acid position 258 according to one embodiment of the present disclosure.
Figure 2:
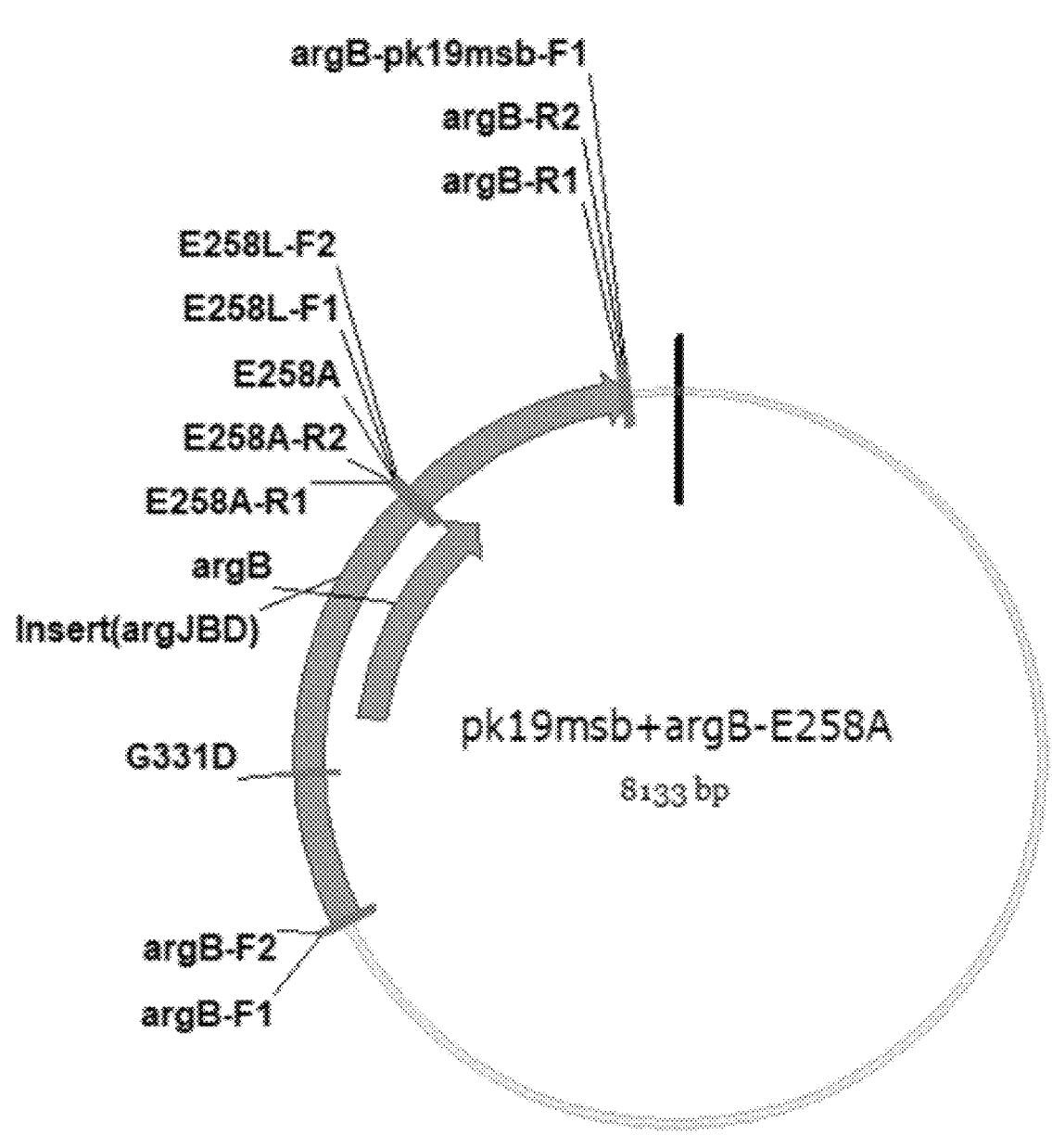
FIG. 2 shows the structure of a pk19msb+argB-E258A vector containing a gene encoding an acetylglutamate kinase fied by PCR and ligated together by overlap PCR, followed by cloning into a pk19msb vector. The resulting plasmid was named pk19msb+argB-E258L (see FIG. 1). To construct the plasmid, the primers shown in Table 1 below were used for amplification of each gene fragment.

More specifically, glutamic acid at amino acid position 258 of the acetylglutamate kinase encoded by the argB gene was substituted with alanine, and the left arm portion (1,614 bp) and the right arm portion (854 bp) with respect to the center of the argB gene on the *Corynebacterium glutamicum* genome were amplified by PCR and ligated together by overlap PCR, followed by cloning into a pk19msb vector. The resulting plasmid was named pk19msb+argB-E258A (see FIG. 2). To construct the plasmid, the primers shown in Table 2 below were used for amplification of each gene fragment.

TABLE 2

| | | Primer (5'→3') | SEQ ID NO |
|---|---|---|---|
| Amplification primers for left homologous arm of argB | argB-F1 | tgattacgcc actgacacggtggataaggaaac | 9 |
| | argB-F2 | actgacacggtggataaggaaac | 10 |
| | E258A-R1 | gccagcaacaccgagt | 17 |
| | E258A-R2 | ggtcaaaagcgccagcaaca | 18 |
| Amplification primers for right homologous arm of argB | E258L-F1 | gcttttgacc atgggtggaattggcacg | 13 |
| | E258L-F2 | atgggtggaattggcacg | 14 |
| | argB-R1 | catcgggaacaacgccat | 15 |
| | argB-R2 | atggtcaccacatcgggaa | 16 |

As a result, *Corynebacterium glutamicum* mutant strain AB2 capable of producing L-arginine was constructed, which has a substitution of alanine for glutamic acid at position 258 in the amino acid sequence of acetylglutamate kinase (SEQ ID NO: 2).

Example 3. Construction of *Corynebacterium glutamicum* Mutant Strain

A *Corynebacterium glutamicum* mutant strain having enhanced activity of acetylglutamate kinase was constructed in the same manner as in Example 1, a recombinant vector (pk19msb+argB-H245D) containing an argB gene encoding an acetylglutamate kinase having a substitution of aspartic acid for histidine at amino acid position 245 was used.

More specifically, histidine at amino acid position 245 of the acetylglutamate kinase encoded by the argB gene was substituted with aspartic acid, and the left arm portion (1,583 bp) and the right arm portion (885 bp) with respect to the center of the argB gene on the *Corynebacterium glutamicum* genome were amplified by PCR and ligated together by overlap PCR, followed by cloning into the recombinant vector pk19msb. The resulting plasmid was named pk19msb+argB-H245D (see FIG. 3). To construct the plasmid, the primers shown in Table 3 below were used for amplification of each gene fragment.

TABLE 3

| | | Primer (5'→3') | SEQ ID NO |
|---|---|---|---|
| Amplification primers for left homologous arm of argB | argB-F1 | tgattacgcc actgacacggtggataaggaaac | 9 |
| | argB-F2 | actgacacggtggataaggaaac | 10 |
| | H245D-R1 | caatgacatcagcagcgctta | 19 |
| | H245D-R2 | atgcggccgtcaatgac | 20 |

TABLE 3-continued

| | | Primer (5'→3') | SEQ ID NO |
|---|---|---|---|
| Amplification | H245D-F1 | acggccgcat cgcgcactcggtgttgct | 21 |
| primers for right | H245D-F2 | cgcgcactcggtgttgct | 22 |
| homologous arm of | argB-R1 | catcgggaacaacgccat | 15 |
| argB | argB-R2 | atggtcaccacatcgggaa | 16 |

As a result, *Corynebacterium glutamicum* mutant strain AB3 capable of producing L-arginine was constructed, which has a substitution of aspartic acid for histidine at position 245 in the amino acid sequence of acetylglutamate kinase (SEQ ID NO: 2).

Experimental Example 1. Evaluation of L-Arginine Productivities of *Corynebacterium glutamicum* Mutant Strains The L-arginine productivities of the *Corynebacterium glutamicum* mutant strains AB1 to AB3 constructed in Examples 1 to 3 were evaluated in comparison with that of the parent strain.

Each strain was patched on a flask solid seed medium and cultured at 30° C. for 24 hours. Each cultured colony was inoculated into a 10-ml flask titer medium and cultured at 200 rpm at 32° C. for 30 hours. The compositions of the media used here are shown in Table 4 below. After completion of the culturing, each culture was diluted 100-fold with distilled water and filtered through a 0.45-μm filter, and then the amount of L-arginine produced was analyzed using high-performance liquid chromatography (HPLC) (Agilent Technologies 1260 Infinity, Agilent Technologies) equipped with a column (DionexIonPac™ CS12A) and a UV detector (195 mm), and the results are shown in Table 5 below. In Table 5, L-arginine (%) denotes the amount (percentage) of arginine produced by each strain, and fermentation yield (Yp/s) (%) denotes the amount of L-arginine produced per glucose consumed.

TABLE 4

| Flask solid seed medium (per L) | 10.5 g of 98% glucose, 1 g of beef extract, 4 g of yeast extract, 2 g of polypeptone, 2 g of NaCl, 40 g of $(NH_4)_2SO_4$ and 20 g of agar |
|---|---|
| Flask titer medium (per L) | 120 g of 98% glucose, 1 g of $MgSO_4$, 2 g of $KH_2PO_4$, 45 g of $(NH_4)_2SO_4$, 20 mg of $FeSO_4$, 20 mg of $MnSO_4$, 100 μg of biotin, 100 μg of thiamine, 4 g of YSP and 2 g of urea |

TABLE 5

| Strain | $OD_{610}$ | L-arginine (%) | Fermentation yield (%) |
|---|---|---|---|
| Parent strain | 35.0 | 1.63 | 16.27 |
| AB1 | 37.0 | 2.53 | 25.32 |
| AB2 | 29.0 | 2.42 | 24.25 |
| AB3 | 32.0 | 2.60 | 26.04 |

As shown in Table 5 above, it was confirmed that the *Corynebacterium glutamicum* mutant strains AB1 to AB3 had significantly increased L-arginine productivity compared to the parent strain due to a substitution of an optimal amino acid for the amino acid at position 258 or 245 in the amino acid sequence of acetylglutamate kinase.

Example 4. Construction of *Corynebacterium glutamicum* Mutant Strain

*Corynebacterium glutamicum* mutant strain CB1 having a substitution of leucine for glutamic acid at position 258 in the amino acid sequence of acetylglutamate kinase (SEQ ID NO: 2) and capable of producing L-citrulline was constructed in the same manner as in Example 1, except that the pk19msb+argB-E258L cloning vector of Example 1-1 was introduced into *Corynebacterium glutamicum* 15GD (KCCM13220P) in place of *Corynebacterium glutamicum* 14GR.

Example 5. Construction of *Corynebacterium glutamicum* Mutant Strain

*Corynebacterium glutamicum* mutant strain CB2 having a substitution of alanine for glutamic acid at position 258 in the amino acid sequence of acetylglutamate kinase (SEQ ID NO: 2) and capable of producing L-citrulline was constructed in the same manner as in Example 1, except that the pk19msb+argB-E258A cloning vector of Example 2 was introduced into *Corynebacterium glutamicum* 15GD in place of *Corynebacterium glutamicum* 14GR.

Example 6. Construction of *Corynebacterium glutamicum* Mutant Strain

*Corynebacterium glutamicum* mutant strain CB3 having a substitution of aspartic acid for histidine at position 245 in the amino acid sequence of acetylglutamate kinase (SEQ ID NO: 2) and capable of producing L-citrulline was constructed in the same manner as in Example 1, except that the pk19msb+argB-H245D cloning vector of Example 3 was introduced into *Corynebacterium glutamicum* 15GD in place of *Corynebacterium glutamicum* 14GR.

Experimental Example 2. Evaluation of L-Citrulline Productivities of *Corynebacterium glutamicum* Mutant Strains The L-citrulline productivities of the *Corynebacterium glutamicum* mutant strains CB1 to CB3 constructed in Examples 4 to 6 were evaluated in comparison with that of the parent strain.

Each strain was patched on a flask solid seed medium and cultured at 30° C. for 24 hours. Each cultured colony was inoculated into a 10-ml flask titer medium and cultured at 200 rpm at 32° C. for 30 hours. The compositions of the media used here are shown in Table 6 below. After completion of the culturing, each culture was diluted 100-fold with distilled water and filtered through a 0.45-μm filter, and then the amount of L-citrulline produced was analyzed using high-performance liquid chromatography (HPLC) (Agilent Technologies 1260 Infinity, Agilent Technologies) equipped with a column (DionexIonPac™ CS12A) and a UV detector (195 mm), and the results are shown in Table 7 below. In Table 7, L-citrulline (%) denotes the amount (percentage) of citrulline produced by each strain, and fermentation yield (Yp/s) (%) denotes the amount of L-citrulline produced per glucose consumed.

TABLE 6

| Flask solid seed medium (per L) | 10.5 g of 95% glucose, 10 g of beef extract, 10 g of yeast extract, 10 g of polypeptone, 2.5 g of NaCl and 100 mg of arginine |
| Flask titer medium (per L) | 105.3 g of 95% glucose, 1 g of $MgSO_4$, 4 g of YPA, 0.8 g of $KH_2PO_4$, 1.2 g of $Na_2HPO_4$, 30 g of $(NH_4)_2SO_4$, 20 mg of $FeSO_4$, 20 mg of $MnSO_4$, 10 mg of $ZnSO_4$, 100 mg of arginine, 100 μg of biotin and 200 μg of thiamine |

TABLE 7

| Strain | $OD_{610}$ | L-citrulline (%) | Fermentation yield (%) |
|---|---|---|---|
| Parent strain | 14.0 | 1.67 | 16.70 |
| CB1 | 16.0 | 1.87 | 18.70 |
| CB2 | 14.0 | 1.91 | 19.10 |
| CB3 | 17.0 | 1.88 | 18.80 |

As shown in Table 7 above, it was confirmed that the *Corynebacterium glutamicum* mutant strains CB1 to CB3 had significantly increased L-citrulline productivity compared to the parent strain due to a substitution of an optimal amino acid for the amino acid at position 258 or 245 in the amino acid sequence of acetylglutamate kinase.

These results suggest that L-arginine and L-citrulline productivities were increased by enhancing enzymatic activity through site-directed mutation in the nucleic acid sequence or amino acid sequence of the acetylglutamate kinase involved in the L-arginine biosynthesis pathway.

So far, the present disclosure has been described with reference to the embodiments. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

[Accession Number]

Depository authority: Korean Culture Center of Microorganisms (KCCM)

Accession number: KCCM13219P

Deposit date: Jun. 29, 2022

Depository authority: Korean Culture Center of Microorganisms (KCCM)

Accession number: KCCM13220P

Deposit date: Jun. 29, 2022

What is claimed is:

1. A *Corynebacterium* sp. mutant strain having increased L-arginine or L-citrulline productivity by having enhanced activity of acetylglutamate kinase, wherein said acetylglutamate kinase of the *Corynebacterium* sp. mutant strain having increased L-citrulline productivity has a substitution of aspartic acid for histidine at amino acid position 245 in the amino acid sequence of SEQ ID NO: 2, wherein said acetylglutamate kinase of the *Corynebacterium* sp. mutant strain having increased L-arginine productivity has a substitution of leucine for glutamic acid at amino acid position 258 or a substitution of aspartic acid for histidine at amino acid position 245 in the amino acid sequence of SEQ ID NO: 2.

2. The *Corynebacterium* sp. mutant strain of claim 1, which is *Corynebacterium glutamicum*.

3. A method for producing L-arginine or L-citrulline comprising steps of:

culturing the *Corynebacterium* sp. mutant strain of claim 1 in a medium; and recovering L-arginine or L-citrulline from the cultured mutant strain or the medium in which the mutant strain has been cultured.

* * * * *